US00PP17275P2

(12) United States Plant Patent
Larsen

(10) Patent No.: US PP17,275 P2
(45) Date of Patent: Dec. 12, 2006

(54) ***OSTEOSPERMUM* PLANT NAMED 'SUNNY MAXIMA'**

(50) Latin Name: *Osteospermum ecklonis (DC) T. Norl.*
Varietal Denomination: Sunny Maxima

(75) Inventor: Bjarne Nyholm Larsen, Odense N (DK)

(73) Assignee: Sunny Osteospermum APS, Odense N (DK)

( * ) Notice: Subject to any disclaimer, the term of this patent is extended or adjusted under 35 U.S.C. 154(b) by 0 days.

(21) Appl. No.: 11/234,246

(22) Filed: Sep. 26, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner LLP

(57) ABSTRACT

A new distinct cultivar of *Osteospermum* plant named 'Sunny Maxima', characterized by its plant height averaging 16 cm, and plant diameter averaging 25 cm; thicker and sturdier stems; large, composite, daisy type inflorescences measuring up to 8 cm in diameter; fully opened inflorescences with striking red-purple ray florets with light red-purple bases and disc florets with gray-purple tips and a light purple basal tube; and mature foliage color of green, RHS 137A (upper side) and yellow-green, RHS 147B (under side).

4 Drawing Sheets

Botanical designation: *Osteospermum ecklonis* (*DC*) *T. Norl.*
Variety denomination: 'Sunny Maxima'.

BACKGROUND OF THE INVENTION

The present invention relates to a new and distinct cultivar of *Osteospermum* plant, botanically known as *Osteospermum eklonis* (*DC*) *T. Norl*., commonly known as Cape Daisy, and hereinafter referred to by the variety denomination 'Sunny Maxima'.

The new *Osteospermum* is a product of a planned breeding program conducted by the inventor, Bjarne Larsen, in Stige, Odense, Denmark. The objective of the breeding program was to develop a new *Osteospermum* cultivar with upright, compact plant habit, interesting inflorescence color, good branching performance, low growth retardant requirements, and low temperature tolerance.

The new *Osteospermum* originated from a planned crossing of two *Osteospermum* selected parent plants made by the inventor in 2003 in Stige, Odense, Denmark. The female or seed parent is an *Osteospermum ecklonis* (*DC*) *T. Norl.* cultivar designated '1.154.93 ' (unpatented). The male or pollen parent is an *Osterospermum ecklonis* (*DC*) *T. Norl.* cultivar designated '998' (unpatented). The new *Osteospermum* cultivar 'Sunny Maxima' was selected by the inventor as a single flowering plant within the progeny of the above crossing in 2003 in a controlled environment in Stige, Odense, Denmark.

Asexual reproduction of the new *Osteospermum* cultivar by apical stem cuttings was first performed in June 2003 in Stige, Odense, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be unique characteristics of 'Sunny Maxima'. These characteristics in combination distinguish 'Sunny Maxima' as a new and distinct cultivar:

1. Plant height averaging 16 cm, and plant diameter averaging 25 cm;
2. Thicker and sturdier stems;
3. Large, composite, daisy type inflorescences measuring up to 78 cm in diameter;
4. Fully opened inflorescences with striking red-purple ray florets with light red-purple bases and disc florets with gray-purple tips and a light purple basal tube; and
5. Mature foliage color of green, RHS 137A (upper side) and yellow-green, RHS 147B (under side).

Plants of the parental cultivars, '1.154.93' (unpatented) and '998' (unpatented) are unavailable to provide a detailed botanical comparison to plants of the new cultivar 'Sunny Maxima'.

Of the many commercial cultivars known to the present inventor, the most similar in comparison to the new *Osteospermum* cultivar 'Sunny Maxima' is *Osteospermum* cultivar 'Sunny Mary' (allowed, U.S. Plant Pat. No. 16,389). In side-by-side comparisons conducted in Stige, Odense, Denmark, plants of 'Sunny Maxima' differed from plants of 'Sunny Mary' in the characteristics described in Tabe 1:

TABLE 1

| Trait | New Cultivar 'Sunny Maxima' | Comparison Cultivar 'Sunny Mary' |
|---|---|---|
| Plant height | About 16 cm | About 18 |
| Plant diameter | About 25 cm | About 18 |
| Number of lateral branches | 2–4 primary, 16–18 secondary (flowering) | 2 primary, 20 secondary |

TABLE 1-continued

| Trait | New Cultivar 'Sunny Maxima' | Comparison Cultivar 'Sunny Mary' |
|---|---|---|
| Lateral branch Length | Primary: 3–5 cm, Secondary: 4–12 cm (including inflorescence) | Primary: 2 cm, Secondary: 12–14 cm |
| Lateral branch diameter | 7–8 mm | 3–5 mm |
| Quantity of leaves per lateral branch | 12–16 | 12 |
| Internode length | 10–12 mm | 10–17 mm |
| Leaf margin | 4 triangular, acute lobes | Broadly lobed, few pointed lobes |
| Mature leaf color | Upper side: RHS 137A Under side: RHS 147B | Upper side: RHS N147A Under side: RHS 148A |
| Number of inflorescences per plant | About 32 | About 37 |
| Inflorescence Diameter | About 8 cm | 4–5 cm |
| Bud Color | From yellow-green, RHS 146B (base) to purple, RHS N79A (apex) | From green, RHS 137B (base) to yellow-green, RHS 150A |
| Ray floret color (Fully opened, upper side) | Red-purple, RHS 72C (apex) to light red-purple, RHS 73D (base) | Red-purple, RHS 67A, with stripes of darker red-purple, RHS 72A |
| Ray floret color (Fully opened, under side) | Gray-purple, RHS 186A, with gray-orange stripes and edges, RHS 176A | Purple, RHS N79A, with purple stripes, RHS N79C |
| Fading color | No fading, withering to RHS 177B, gray-orange | No fading, withering to RHS 79A, purple |
| Phyllaries | 18 lanceolate units fused basally | 15 lanceolate units fused basally |
| Anthers color | Dark purple, RHS 97A | Black, RHS 202A |
| Stigma color | Purple | Yellow, RHS 16C, yellow-orange. |

BRIEF DESCRIPTION OF THE PHOTOGRAPHS

The accompanying colored photographs illustrate the overall appearance of the new *Osteospermum* cultivar 'Sunny Maxima' showing the colors as true as is reasonably possible with colored reproductions of this type. Colors in the photographs may differ slightly from the color values cited in the detailed botanical description which acccurately describe the color of the new *Osteospermum* cultivar 'Sunny Maxima'.

DETAILED BOTANICAL DESCRIPTION

Figure 1:
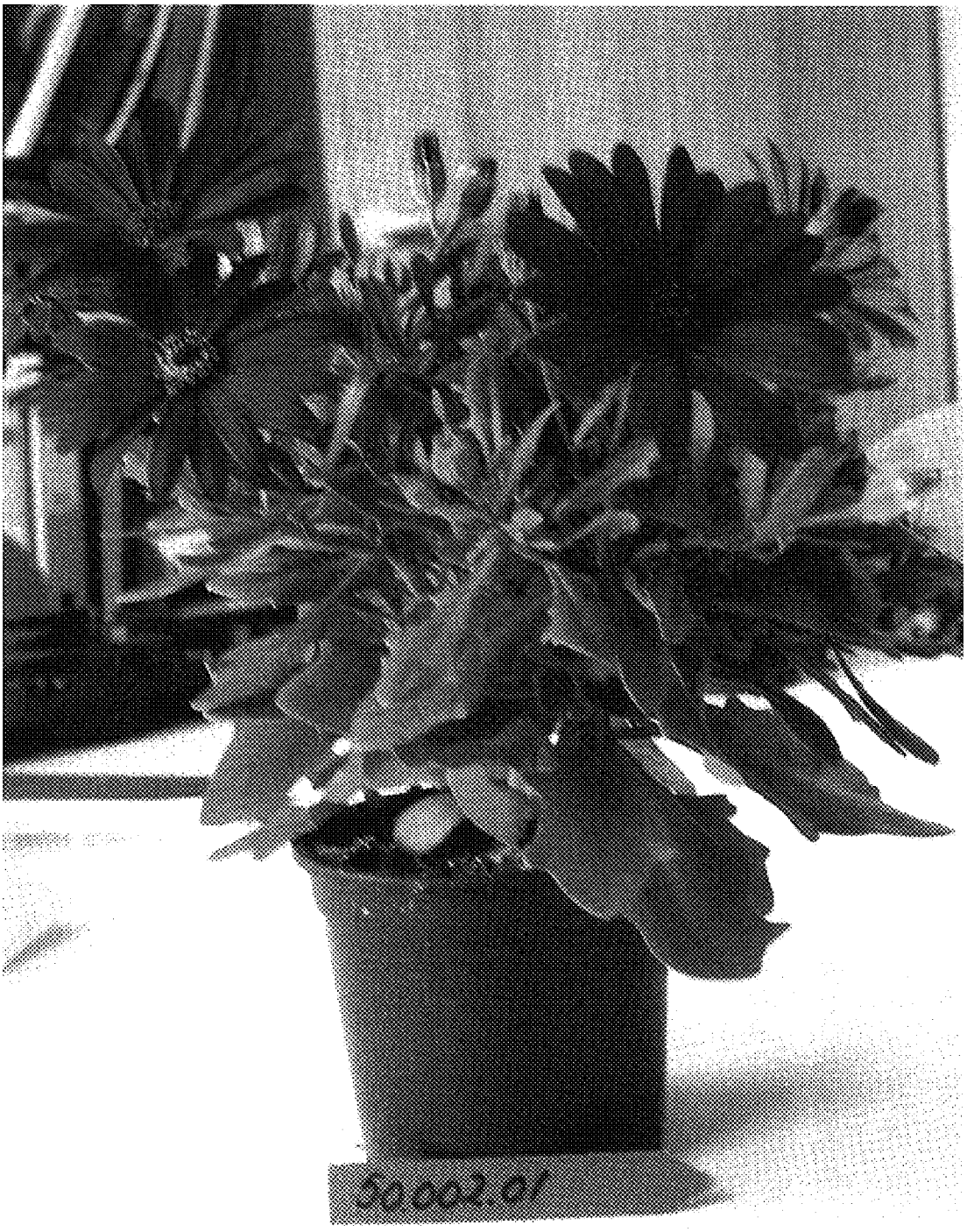
FIG. 1 shows a side perspective view of a typical potted flowering plant of 'Sunny Maxima' (labelled with the Breeder's reference 50.002.01), as a produced cultivar, 20 weeks after planting.
Figure 2:
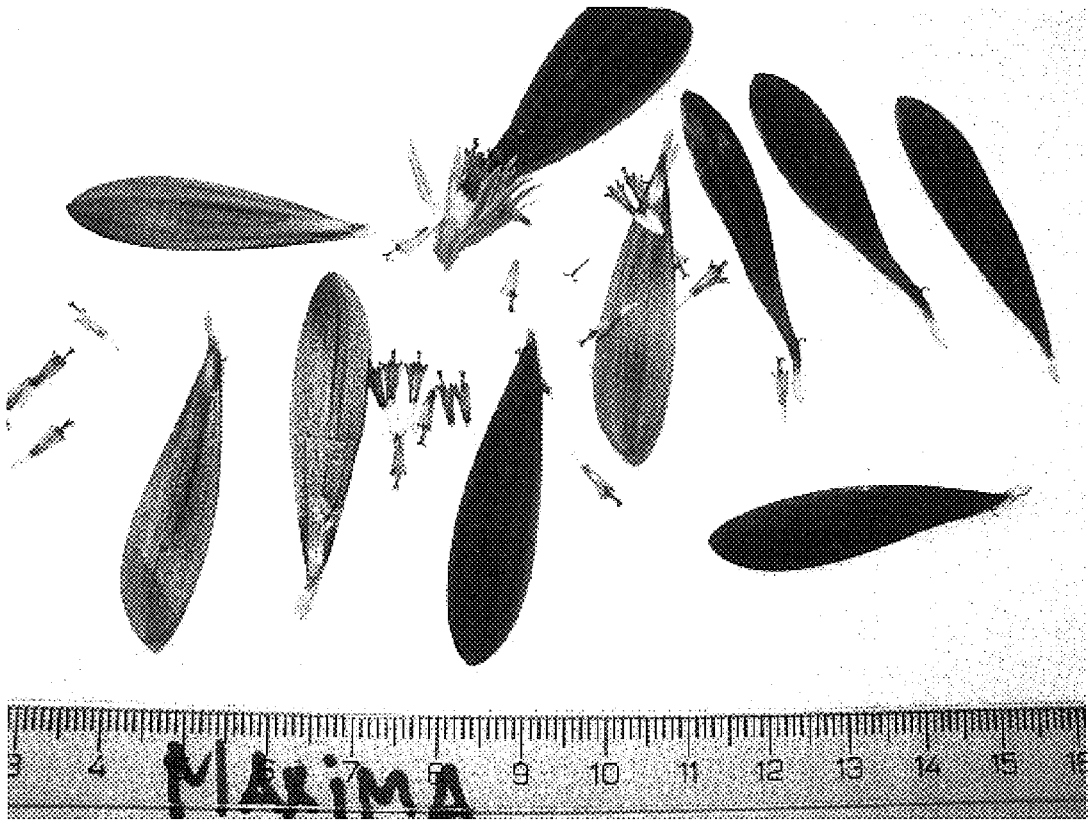
FIG. 2 shows a dissected view of a typical inflorescence of 'Sunny Maxima', as a produced cultivar, 20 weeks after planting.
Figure 3:
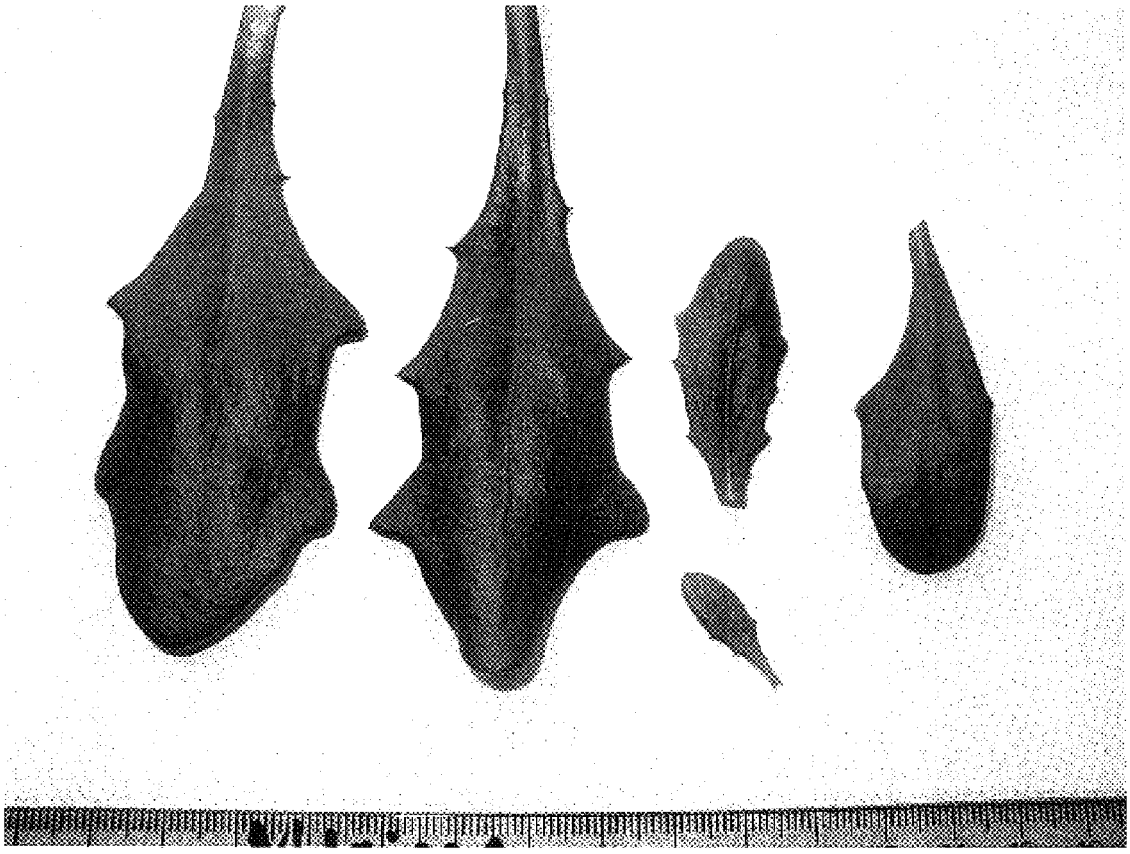
FIG. 3 shows a view of different leaf forms and sizes of 'Sunny Maxima', as a produced cultivar, 20 weeks after planting.
Figure 4:
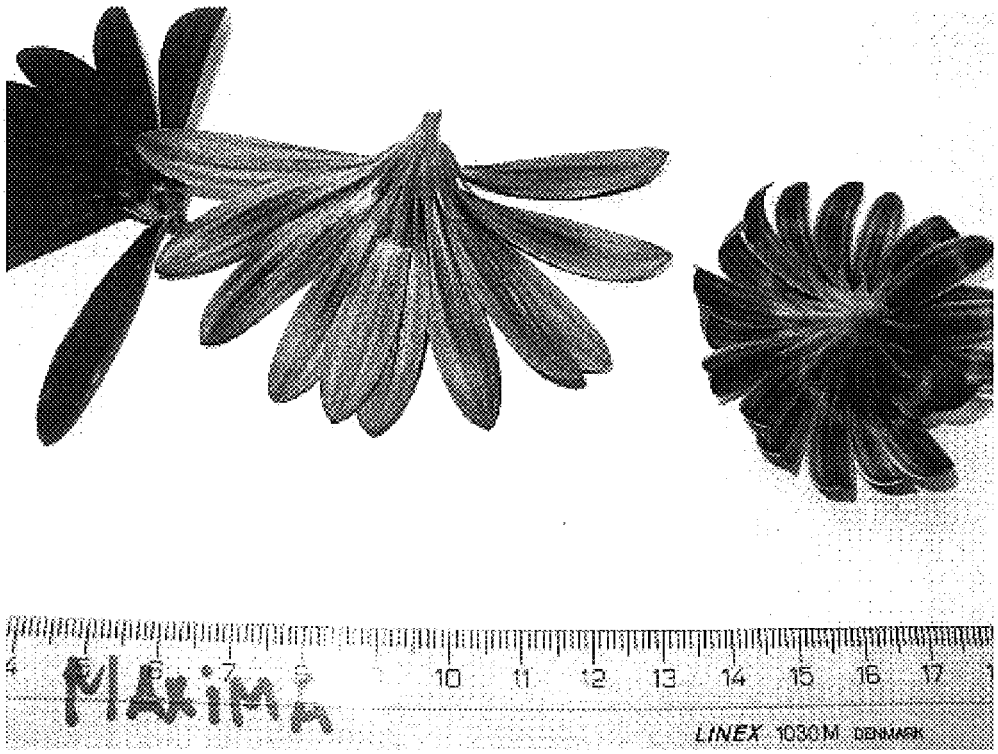
FIG. 4 shows a bottom view of the inflorescences of 'Sunny Maxima', as a produced cultivar, 20 weeks after planting.
Figure 5:
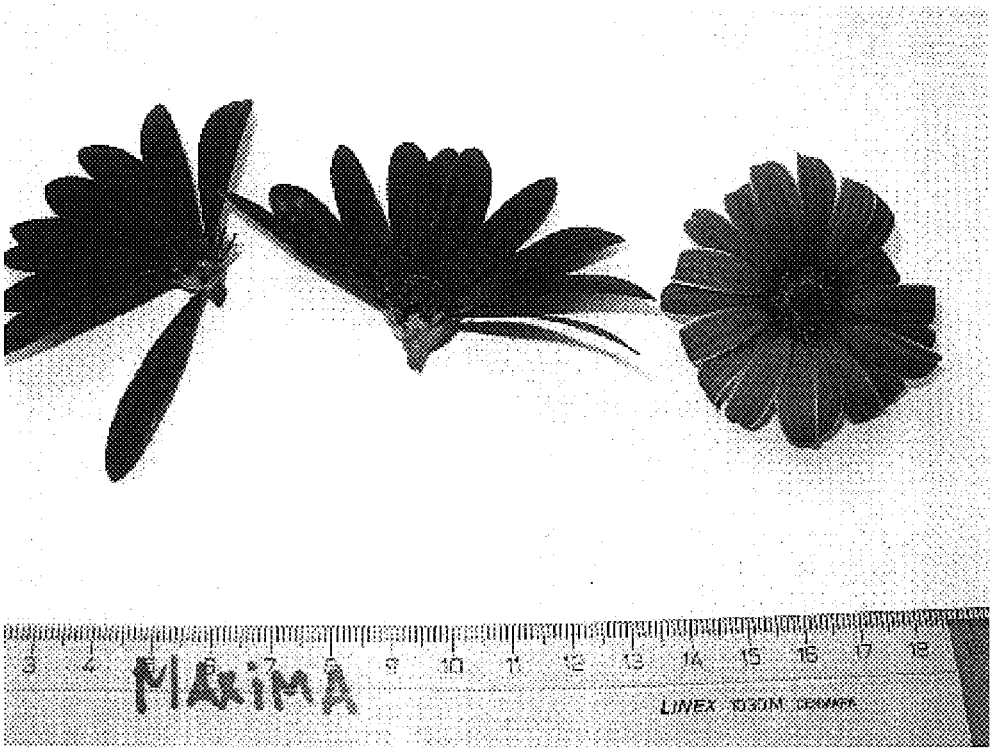
FIG. 5 shows a top view of the inflorescences of 'Sunny Maxima', as a produced cultivar, 20 weeks after planting.

The new *Osteospermum* cultivar 'Sunny Maxima' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new *Osteospermum* cultivar 'Sunny Maxima' as grown in a greenhouse and outside in Stige, Odense, Denmark, under conditions which closely approximate those generally used in commercial practice and garden use. Vegetative propagation with apical tip cuttings (4–5 leaves) took place in a greenhouse with propagation tents for about 3 weeks with the day and night temperature averaging about 20° C. The temperature was then lowered to the day and night temperature averaging about 14° C. The plants were subirrigated with a nutrient solution of 2–3 mS when needed and given supplementary irradiation with SON T lamps having an installed energy level of 400 $Wm^2$.

Color references are made to The Royal Horticultural Society Colour Chart (R.H.S), 4 $^{th}$ edition 2000, except where general colors of ordinary significance are used. The photographs and descriptions were taken during the spring season when outdoor day temperatures ranged from 7° C. to 15° C. and outdoor night temperatures ranged from 0° C. to 7° C. The age of the plants described is 20 weeks.

Botanical classification: *Osteospermum ecklonis* (*DC*) *T. Norl.*

Parentage:

*Female or seed parent.*—*Osteospermum ecklonis* (*DC*) *T. Norl.* designated '1.154.93' (unpatented).

*Male or pollen parent.*—*Osteospermum ecklonis* (*DC*) *T. Norl.* designated '998' (unpatented).

Propagation:

*Type.*—Apical stem cutting.

*Time and temperature to initiate roots.*—Summer: About 12 to 14 days at to 20° C. to 22° C. in tunnels in a greenhouse. Winter: About 17 to 20 days at 20° C. to 22° C. in tunnels in a greenhouse.

*Time and temperature to develop roots*—Summer: About 14 to 18 days at 20° C to 22° C. in tunnels in a greenhouse. Winter: About 20 to 22 days at 20° C. to 22° C. in tunnels in a greenhouse.

*Rooting description.*—100 % rooting.

*Rooting habit.*—Fine, fibrous and branching.

*Root color.*—White, RHS 155D.

*Root Texture.*—Coarse.

Plant description:

*General appearance and form.*—Perennial plant with upright plant habit and used as a bedding or potted plant. Plant non-hardy as a bedding plant. *Osteospermum* inflorescences in composite heads, daisy type.

*Growth and branching habit.*—Freely branching with lateral flowering branches forming at every node; dense and bushy. Basal branching and pinching required.

*Growth rate/vigor.*—Vigorous.

*Plant height* (*soil level to top of plant plane*).—About 16 cm, Range: 14–17 cm.

*Plant width* (*spread*).—About 25 cm, Range 20–28 cm.

*Plant strength.*—Low temperature tolerance: Withstands temperatures down to +1° C. High temperature tolerance: Up to +35° C. but flowering may cease.

*Crop time to produce a mature flowering plant.*—After rooting, about 20 weeks are required to produce finished flowering plants in 11 cm pots.

Branches:

*Number of branches per plant.*—2–4 primary, 16–18 secondary.

*Length.*—Primary: About 3–5 cm. Secondary: 4–12 cm (including inflorescence).

*Diameter.*—About 7–8 mm.

*Internode length.*—About 10–12 mm.

*Strength.*—Very strong.

*Aspect.*—Upright, branches at 45° angle.

*Texture.*—Glabrous.

*Color*—Yellow-green, RHS 144B, with spots of gray-purple, RHS 184C.

Foliage description:

*Arrangement.*—Alternate (5-whorl), single, entire, lobed, ovate to spatulate.

*Length.*—About 3–8 cm.

*Width.*—About 1–3 cm.

*Overall shape of leaf.*—Ovate to spatulate.

*Shape at apex.*—Mature leaf: Rounded. Young leaf: Acute.

*Shape at base.*—Attenuate, decurrent.

*Margin.*—Entire, 4 triangular, acute lobes.

*Texture.*—Scattered, short stiff hairs along veins and edges.

*Color of developing foliage.*—Upper surface: RHS 146C, yellow-green. Lower surface: RHS 148C, yellow-green.

*Color of mature foliage.*—Upper surface: RHS 137A, green. Lower surface: RHS 147B, yellow-green.

*Venation pattern.*—Brochidodromus, form of pinnate.

*Venation color.*—RHS 148B, yellow-green.

*Petiole length.*—About 10–35 mm.

*Petiole diameter.*—About 2–6 mm (flat, winged).

*Petiole texture.*—Upper surface: Glabrous. Lower surface: Glabrous, with scattered short stiff hairs.

*Petiole color.*—Upper surface: RHS 145B, yellow-green. Lower surface: RHS 145C, yellow-green.

Inflorescence description:

*Appearance.*—Terminal and axillary inflorescences held above and beyond the foliage. Single, composite inflorescence form, radially symmetrical, with flat lanceolate, ligulate ray florets and tubular disc florets massed at the center, ray and disc florets arranged acropetally on a capitulum. Inflorescences face upright with aspect of 60° angle.

*Natural flowering season.*—Continuous throughout the spring and summer in temperate regions. Season can be extended by vernalization and long day treatments. Flowering may cease if night temperatures exceed +25° C. for several weeks.

*Time to flower.*—7 to 14 days (longevity of individual inflorescences is dependent on temperature and light conditions).

*Postproduction longevity.*—Inflorescences maintain good color and substance for about 14 days on the plant when grown in an outdoor environment. Inflorescences persistent, but wither to almost insignificance.

*Quantity of inflorescences.*—Freely flowering; more than 30 open inflorescences and inflorescence buds per plant.

*Rate of inflorescences opening.*—About 3 per week per plant, depending on light and temperature conditions.

*Fragrance.*—Flowers have a weak, fresh lemon scent.

Bud:

*Rate of opening (from showing color to fully open inflorescence).*—4 to 6 days.

*Quantity per lateral stem.*—About 9 to 13.

*Length.*—About 0 to 20 mm at color showing.

*Diameter.*—About 0 to 10 mm.

*Shape.*—Globular until color, then ovoid.

*Color.*—From RHS 146C, yellow-green (base) to RHS N79A, purple (apex).

Peduncle:

*Length.*—Terminal: About 7 cm. Secondary: About 6 cm. Tertiary: About 5 cm.

*Diameter.*—About 2 mm.

*Appearance and angle.*—Terminal: Erect, 5 to 10 degrees from vertical. Secondary: About 30 to 45 degrees from vertical. Tertiary: About 30 to 45 degrees from vertical.

*Strength.*—Strong.

*Texture.*—Glabrous.

*Color.*—RHS 144C, yellow-green.

Inflorescence:

*Inflorescence depth (height).*—About 6 mm.

*Inflorescence diameter.*—About 8 cm.

*Receptacle diameter.*—About 13 mm.

*Receptable height.*—About 14 mm.

*Receptacle shape.*—Conical (inverted).

*Receptacle color.*—RHS 145D, yellow-green.

Ray florets:

*Quantity per inflorescence.*—Typical number: 20, overlapping, in 1½ whorl. Observed number: 19–22.

*Length.*—About 30 mm, Range: 28–32.

*Width.*—About 9 mm, Range: 8–10 mm.

*Overall shape.*—Elliptic (Flat lanceolate, ligulate).

*Shape at apex.*—Acute with slight retuse tip.

*Shape at base.*—Attenuate.

*Margin.*—Entire.

*Texture.*—Upper surface: Velvety. Lower surface: Shiny.

*Orientation.*—Initially 20 degrees from vertical, with development, close to 0 degrees from vertical.

*Color (when opening).*—Upper side: RHS N75C, purple (apex) to RHS 75D(base). Under side: Gray-purple center stripe, RHS 186A with stripes of gray-red, RHS 182B, and few spots and edges with gray-red, RHS 179C.

*Color (when fully opened).*—Upper side: Red-purple, RHS 72C (apex) to light red-purple, RHS 73D. Under side: Gray-purple, RHS 186A, with gray-orange stripes and edges, RHS 176A.

Disc florets:

*Quantity per inflorescence.*—Typical number: 80. Observed number: 74–90.

*Length.*—About 6 mm.

*Width.*—At apex: About 2–3 mm. At base: About 1–2 mm.

*Disc area diameter.*—About 13 mm.

*Overall shape.*—Tubular.

*Shape at apex.*—Star with 5 triangular tips.

*Shape at base.*—Fused to tube.

*Margin.*—Entire.

*Texture.*—Glabrous.

*Color (when opening).*—Upper and under side: RHS N79A, dark purple.

*Color (when fully opened).*—Upper and under side: RHS 183A, gray-purple (apex), and basal tube RHS 76D, light purple.

Phyllaries:

*Quantity per inflorescence.*—18 lanceolate units.

*Length.*—About 6 to 12 mm.

*Width.*—About 1–3 mm.

*Overall shape.*—Lanceolate, basally fused.

*Shape at apex.*—Acuminate.

*Shape at base.*—Fused.

*Margin.*—Entire.

*Color.*—Upper surface: RHS 144D, yellow-green. Lower surface: RHS 144C, yellow-green.

Reproductive organs:

Androecium: On disc florets only.

*Stamen number.*—5 per floret; fused around style.

*Stamen length.*—About 2 mm.

*Anther shape.*—Linear.

*Anther length.*—About 1 mm.

*Anther color.*—RHS 97A, dark purple.

*Pollen amount.*—Abundant

*Pollen color.*—RHS N25A, orange.

Gynoecium: On ray and disc florets.

*Quantity.*—1 per floret.

*Pistil length.*—About 4 mm.

*Stigma shape.*—Brush-like.

*Stigma color.*—Purple.

*Style length.*—About 2 mm.

*Style color.*—RHS 155B, white.

*Ovary color.*—RHS 2D, green-yellow.

Seed: None observed at this stage of development.

Fruit: None observed.

Disease/pest resistance: Good.

Disease/pest susceptibility: No diseases or pests observed.

Temperature tolerance: Plants of the new *Osteospermum* have exhibited good tolerance to draught, rain and wind; however, flowering may cease during hot periods (when night temperatures exceed above 25° C.). Low temperature tolerance to 1° C.

Growth retardant(s): 3 times 0.2% Chlormequat drench during production.

I claim:

1. A new and distinct cultivar of *Osteospermum* plant named 'Sunny Maxima', as illustrated and described herein.

* * * * *